United States Patent
Phillips et al.

(10) Patent No.: US 7,185,597 B1
(45) Date of Patent: Mar. 6, 2007

(54) METHOD FOR MANUFACTURING A MEDICAL IMPLANT

(75) Inventors: Peter Phillips, Badsey (GB); Gail Beaton, Henley-on-Thames (GB)

(73) Assignee: Anson Medical Limited (GB)

( * ) Notice: Subject to any disclaimer, the term of this patent is extended or adjusted under 35 U.S.C. 154(b) by 718 days.

(21) Appl. No.: 10/111,795

(22) PCT Filed: Oct. 27, 2000

(86) PCT No.: PCT/GB00/04153

§ 371 (c)(1),
(2), (4) Date: Jul. 23, 2002

(87) PCT Pub. No.: WO01/30269

PCT Pub. Date: May 3, 2001

(30) Foreign Application Priority Data

Oct. 27, 1999 (GB) ................................. 9925447.6

(51) Int. Cl.
*D05B 21/00* (2006.01)
*A61F 2/02* (2006.01)
*D05B 39/00* (2006.01)

(52) U.S. Cl. ............................. 112/475.04; 112/475.08; 600/36; 623/901

(58) Field of Classification Search ........... 112/470.12, 112/103, 470.14, 470.33, 63, 475.01, 475.04, 112/475.08, 475.17; 606/151, 213, 219, 606/194; 623/1.11, 9.01, 1.15, 1.23, 901; 600/30, 36
See application file for complete search history.

(56) References Cited

U.S. PATENT DOCUMENTS

| | | | |
|---|---|---|---|
| 4,241,681 A | 12/1980 | Porter | |
| 4,502,159 A | 3/1985 | Woodroof et al. | |
| 4,503,788 A * | 3/1985 | Giannuzzi et al. | 112/470.06 |
| 5,406,900 A * | 4/1995 | Schramayr et al. | 112/2 |
| 5,824,037 A | 10/1998 | Freislinger et al. | |
| 5,824,040 A | 10/1998 | Freislinger et al. | |
| 5,893,856 A | 4/1999 | Jacob | |
| 5,988,085 A * | 11/1999 | Martz | 112/470.13 |
| 6,197,143 B1 * | 3/2001 | Bodnar | 156/218 |
| 6,295,940 B1 * | 10/2001 | Shonteff | 112/63 |
| 6,352,561 B1 * | 3/2002 | Leopold et al. | 623/1.23 |
| 6,401,641 B1 * | 6/2002 | Miyano | 112/470.05 |
| 6,447,524 B1 | 9/2002 | Knodel | |
| 6,685,625 B2 * | 2/2004 | Gabbay | 600/36 |

FOREIGN PATENT DOCUMENTS

WO    WO 99 37242 A    7/1999

* cited by examiner

*Primary Examiner*—Ismael Izaguirre
(74) *Attorney, Agent, or Firm*—Craig A. Fieschko, Esq.; DeWitt Ross & Stevens S.C.

(57) ABSTRACT

A method for stitching thread onto the wall of a tubular medical implant (preferably a graft) employs a sewing machine with an elongate bobbin or a needle on an elongate element, depending on whether it is desired to sew from the outside-in or the inside-out. A motor rotates and translates the implant, which is mounted on a hollow drum, relative to the needle.

10 Claims, 3 Drawing Sheets

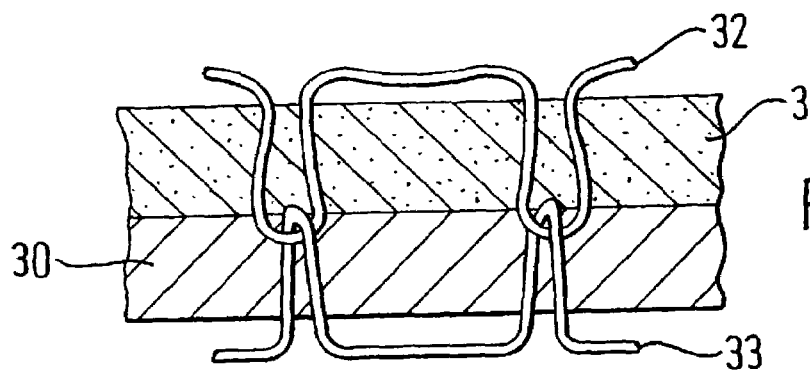
FIG. 3
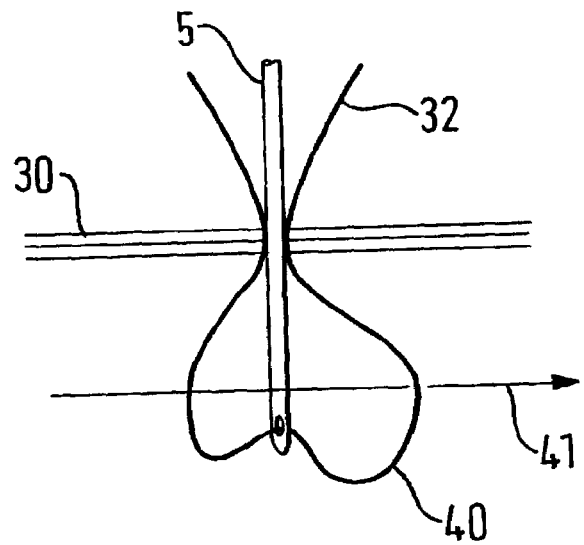
FIG. 4
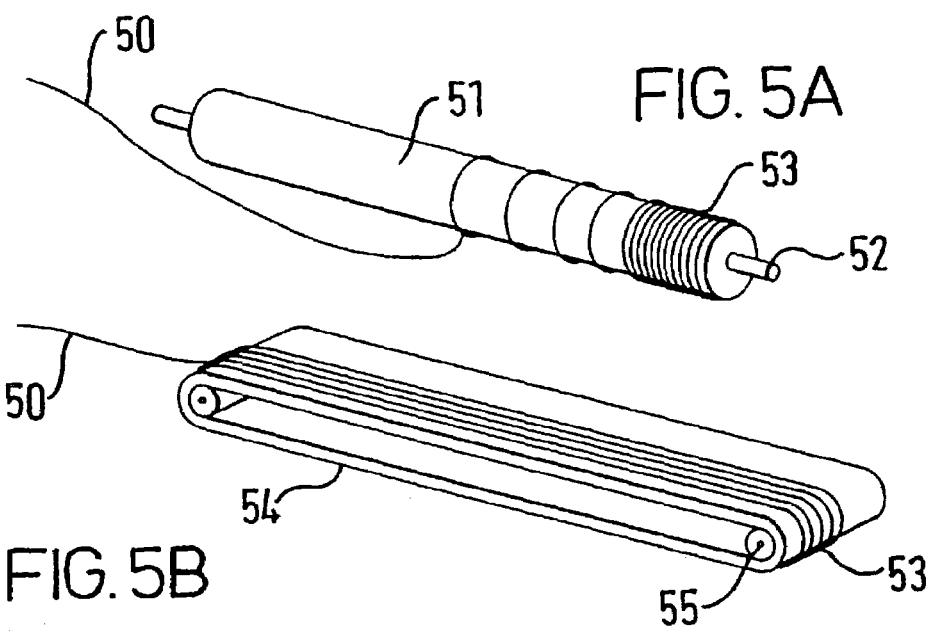
FIG. 5A
FIG. 5B

METHOD FOR MANUFACTURING A MEDICAL IMPLANT

FIELD OF THE INVENTION

The present invention relates to a method and apparatus for stitching thread to the wall of a tubular medical implant, and in particular to a method and apparatus for stitching thread to the wall of a graft, for example to form a graft-stent.

BACKGROUND OF THE INVENTION

Typically, tubular grafts are stitched by hand to metallic stent structures and this process can take a long time. Other problems with the process include difficulties in controlling and assuring the quality and the cost of the final product.

An alternative solution has been described in WO 99/37242 (in the name of the present applicant) in which computerized embroidery is used to manufacture a flat-form device which is subsequently rolled into a tube. This approach solves many of the issues associated with hand manufacturing but results in a seam and prevent some continuous structures from being designed.

GB 2165559 (University College London) discloses a sewing machine for forming stitches in a substrate, for example body tissue, during surgery. The sewing machine employs suction to pull a folded section of the substrate into the machine so that it is disposed between a needle and a hook. The needle can then be used to feed thread through the folded section of substrate to emerge the other side, and to engage the thread on the hook. This action is repeated with the sewing machine being moved along the substrate, thereby forming stitches in the substrate. This sewing machine could not be employed to stitch thread to the wall of a tubular graft, because the graft would not be sufficiently compliant to enable a folded section of graft to be sucked into the machine.

U.S. Pat. No. 4,502,159 (Shiley Incorporated) discloses a method for forming a tubular prosthesis by rolling pericardial tissue into a tube and stitching along the tube to form a longitudinal seam. However, the stitches are formed conventionally by passing a thread from one side of the seam to the other on the outside of the tube.

U.S. Pat. No. 4,241,681 (Porter) discloses a sewing machine for sewing a series of spaced reinforcing rings on a long flexible tube of fireproof fabric. The machine comprises a long tubular support over which the work piece is pulled like a sleeve on an arm. A fixed stitching mechanism is provided for forming chain stitch in the work piece, and a puller mechanism advances the work piece over the support as the stitches are formed therein.

U.S. Pat. No. 4,414,908 (Janome Sewing Machine Co., Limited) discloses a suturing machine for suturing incised parts of a patient. The machine comprises a needle holder (effectively a pair of pliers) and a shuttle holder which is slideably mounted on the needle holder. This means that movement of the needle independently of the shuttle is not possible for all degrees of freedom. In an alternative embodiment, the needle is rotatable circumferentially around the shuttle. The apparatus is not suitable for sewing a tubular implant.

SUMMARY OF THE INVENTION

In accordance with a first aspect of the invention, there is provided a method for stitching thread to the wall of a tubular medical implant, comprising the steps of mounting the implant on an implant support, rotating and translating the implant support about and along its longitudinal axis in order to position a needle at any desired location over the implant surface, operating the needle to feed a first thread from a first side of the implant wall through the implant wall, forming a first loop of the first thread on the second side of the implant wall, passing thread through said loop, and pulling said loop closed to form a stitch, wherein the step of passing thread through said loop is carried out by means for passing thread through said loop, said means being driven back and forth along the longitudinal axis of the implant.

This method enables a chain stitch to be formed in a graft wall by passing the first thread through the graft wall again to form a second loop, and passing this second loop through the first loop prior to pulling the first loop closed. A third loop of the first thread can then be passed through the second loop and the process repeated to form the chain stitch.

Alternatively, a second thread can be passed through the first loop of the first thread and then passed through subsequent loops of the first thread which have been fed through the wall of the graft, in order to form a lock stitch in the graft wall.

Although the invention has been defined in terms of applying thread to a tubular medical implant, which can comprise a graft, a stent, a graft-stent, a graft fixation device, ophthalmic orbital reinforcement devices, annuli for heart valve supports, vein implants, vein valve supports or any other tubular medical form, it will be appreciated that the method and apparatus of the invention can equally be employed to stitch thread to the surface of any tubular form.

In accordance with the second aspect of the present invention, there is provided for stitching thread to the wall of a tubular medical implant, comprising a support for the implant, a needle for feeding a first thread from a first side of the implant wall through the implant wall to form a first loop of thread on the second side of the implant wall, and means for passing thread through said loop from the second side of the implant wall, wherein the apparatus additionally comprises at least one drive mechanism for rotating and translating the implant support about and along its longitudinal axis in order to position the needle at any desired location over the implant surface and a further drive mechanism for driving said means for passing thread through said loop back and forth along the longitudinal axis of the implant.

If it is desired to sew from the inside of the graft out, then the needle may be mounted on an elongate element, so as to be operable from outside the graft but to operate from inside the graft. Alternatively, if it is desired to apply stitches to the graft wall from the outside in, then a conventional needle can be employed and an elongate element is provided for passing thread through the loops on the inside of the graft, the elongate element being operable from outside the graft. Preferably, the elongate element comprises an elongate bobbin or hook.

In a preferred embodiment, the apparatus in accordance with the invention additionally comprises means for rotating the graft relative to the needle about the longitudinal axis of the graft and means of translating the graft relative to the needle along said axis. The graft support is preferably a hollow drum assembly for supporting the graft at either end.

The invention preferably comprises a specialized machine which is capable of sewing on the surface of a cylinder under numeric or computer control and which allows, a number of devices to be constructed which have hitherto been impossible to make with adequate quality, reliability and cost constraints.

The machine most preferably comprises the following principal components:
- A hollow drum assembly which supports the tubular implant at either end.
- Two drive mechanisms which control the angular position of the drum and its axial position
- A sewing machine head which has been adapted to sew from the outside to the inside of a narrow tube.

Thus the mechanism is capable, by means of axial translation or rotation of the cylinder which supports the implant, of placing the sewing machine head at any desired position over the surface of the implant. The implant is likely to be frusto-conical, i.e., it will have different diameters at either end but parallel sided implants will be possible. Tubes with a multiplicity of diameters at different points along the axis can be manufactured to meet particular anatomical criteria.

Normal sewing machines are not suitable for use in this application because the internal diameter and length of the implants are too small to allow a conventional bobbin mechanism to pass through the lumen of the implant so as to lie opposite the needle of the sewing machine. Implants may be as small as 3 mm in diameter and as large as 45 mm in diameter. Preferred sizes are in the range 10 mm to 30 mm in diameter. Implants may be up to 500 mm long with a preferred length of 250 mm.

In one embodiment a chain stitch sewing machine is employed in which a simple mechanism is used beneath the fabric to hook the single thread, which passes through the needle. The hooked thread is then pulled through with the subsequent stitch so that a continuous run of stitches is formed from a single thread. Chain stitch is associated with a tendency to fray or to come apart. As part of the sewing algorithm, the machine can be made to back-stitch or otherwise over-stitched to lock the stitch into place. Glues may also be used to stabilize the thread.

Other methods of stabilizing chain stitch can be employed such as the so-called double chain stitch in which a second thread is introduced. In one version of double chain stitch, alternate loops are formed from alternate threads. In another version, the second thread is pulled through the loops to lock them together. In a further modification to stabilize a chain stitch, a single chain stitch can be formed and upon withdrawing the needle it is rotated between half a turn and five turns to form a twist in the thread. This twist will resist the 'fraying' of the single chain stitch.

In an alternative embodiment a lock stitch sewing machine is employed in which a special design of bobbin is incorporated. In this case the bobbin is long and thin and carries the second thread used in the lock stitch. The bobbin can be wound circumferentially or end-over-end and an appropriate shell is used to draw the yarn off the bobbin. Such designs are feasible in this application of machine because the bulk of stitching used in any single device will be small by comparison with sewing machines used for industrial processes in the clothing industry. Moreover, the stitching speed of the machine is not required to be high because of the small size of the implants and this allows longer bobbins and bobbins of higher mass to be used than would be possible with conventional machines. The mechanism used to traverse the bobbin through the loop formed in the needle thread requires that the bobbin is preferably fired by means of mechanical impulse, compressed air, spring energy, magnetic repulsion or similar means along the axis of the implant.

When the diameter of the graft being sewn is small, the size of thread loop formed by the needle can be sufficiently small as to make it difficult to pass a bobbin through the loop. This problem can be eased by forming a cranked needle which provides a defined gap between its body and the thread. An further alternative design involves the needle puncturing the wall of the graft at an oblique angle to the axis of the graft, again drawing into the graft a length of thread which is not limited to the diameter of the graft. Conveniently in such an arrangement, the angle made between the needle and the axis of the graft can be controlled automatically so that at the beginning and end of a stitch the needle is adjusted to be perpendicular to the axis of the graft, thereby throwing the thread loop into a known position.

An alternative arrangement for a sewing machine capable of sewing onto the surface of the tube involves reversing the positions of the components described above so that the needle is inside the graft and the hook or bobbin lies outside the tube. In this embodiment, the needle may be supported upon a suitable slender beam. The beam and needle are moved relative to the fabric wall of the graft, causing the needle to puncture the wall. If forming a chain stitch, a hook can be used outside the graft to form a loop in the thread carried by the needle. If forming a lock stitch, the bobbin assembly can be mounted on the outside of the implant, permitting a larger bobbin to be used. In the case of forming lock stitch, an additional hook can be used outside the graft to enlarge the thread loop through which is passed the bobbin.

All designs of the sewing machine may benefit from the use of a support (a 'foot') which supports the fabric in the region of the needle puncture. Such a support can be formed from a cylinder in whose wall a hole is made which lies under the needle. Alternatively, the wall of the cylinder may contain a full length slit. Many other embodiments of the support are possible; for instance a partial or complete ring could be positioned under the needle.

In all versions of the sewing machine, a certain latitude is possible in the design of the components that lie within the graft if the tubular graft is distorted to have an oval cross section. When the major axis of the said section is aligned with the needle, a greater length of thread can be drawn into the lumen of the graft, easing the passage of a bobbin. Alternatively, when the minor axis of the said section is aligned with the needle, a wider, flatter bobbin assembly can be used.

While wires and other structures to be sewn to the graft can be temporarily held in place by pins, tacking stitches, glues or similar means, the sewing machine is preferably adapted to have a holder which will keep the structures in proximity with the graft. Such a holder can consist of a cylindrical or conical tube, preferably with a slit in its wall and made of sufficiently elastic material that it can be opened and wrapped around the said structures and graft.

Either preferred design of tubular sewing machine will yield a machine in which stitches can be placed on the surface of a cylinder under the complete control of a computer or similar numerical control device. Such control can be completely pre-programmed or, with the aid of a suitable sensor such as a vision system or an optical switch, the path followed by the stitching can be made to follow a mark or structure already existing on the surface of the graft. This will permit a number of textile processes to take place:
  Tubes can be joined end to end by stitching.
  Tubes can be formed by stitching the seam formed by the edges of a single sheet of material rolled to form a tube.

Stitches of filamentous material can be stitched with any orientation over the surface of the tube.

Material can be attached to the surface of the tube by stitching over it. Such material can include robust filamentous material such as wires which are attached with single or groups of stitches placed on either side of the wire. Larger pieces of material, such as patches can be attached by stitching around their periphery. Larger pieces of material can include tubes which can conduct fluids to other parts of the device or which can be rigidized by pressurization.

Pseudo-lacework can be created in a tubular form by stitch yarn onto a substrate which is subsequently removed by dissolving or other disintegration process. After said process, the stitched yarn remains in place.

Pre-formed structures, such as wire stents, can be attached to the fabric tube by placing them on the tube and employing the inventive apparatus to position the stitches about the components of the stent.

Considering the example of the graft stent, wire can be stitched to the surface of a textile tube to reinforce the tube. In its simplest form, wire can be wrapped around the tube following a helical path without any prior forming of the wire having taken place other than it being nominally straight or curved with a large radius of curvature. In this case, once the wire is attached by stitching around the tubular implant, the wire will be pre-stressed. The resultant implant has the characteristics of the textile tube but with significantly higher radial stiffness, radial expansion after compression such as occurs after passing through a catheter and the ability for the entire implant to be bent back on itself without kinking or collapse.

Wire can be formed in situ by applying a large current or similar heating means across a short section of wire just prior to stitching it to the device. This will locally anneal it to allow the sewing process to form the shape of the wire.

Preferred wires for use in such a machine include nickel/titanium shape memory alloy, stainless steels, Elgiloy and similar highly durable alloys.

Alternatively, pre-shaped wire can be stitch to the surface of the implant. Zig-zags of the form described in WO 99/37242 can be applied to a tubular implant, providing the benefits described above coupled with resistance to axial compression.

When the sewing machine is designed to take more than one needle thread, yarns with different characteristics can be used. Elastic properties can be applied locally by applying yarns made from elastomers, polymers & co-polymers such as polysiloxane. Similarly, tissue adhesives can be drawn into yarns and applied to the surface of the implant. This provides a zone of highly effective sealing to the intimal surface of the vessel in which the device has been implanted.

In a third aspect of the present invention, there is provided a method for forming a medical implant (such as a graft), comprising the steps of stitching the thread on to a soluble substrate which is in the shape of an implant or of a precursor which can be formed in to an implant, dissolving the substrate to leave an implant or precursor formed from said thread, and forming the precursor into an implant. The step of stitching thread on to the soluble substrate is preferably carried out by means of a method defined herein.

The substrate is preferably a light-weight fabric such as a gauze, or it can be soluble. In either case, the cylindrical sewing machine described above will create a tubular implant in which the textile fibers have been distributed to match the mechanical and physiological needs of the implant. Thus fenestrations can be left to allow blood to escape through the walls of the implant into side arteries. These fenestrations can be made without risk of fraying at their edges. Similarly, reinforcing sections can be built up without separate components being added to the device. Wire reinforcements can be included in the wall of the device and can be hidden from either the intimal or visceral surfaces of the device if required. Using the materials suggested above, the implant can be fabricated to have elastic sections, tissue gluing sections, reinforced sections, fenestrated sections. Yarns can be incorporated which release drugs or other pharmacological agents over the surface of the implant.

BRIEF DESCRIPTION OF THE DRAWINGS

A number of preferred embodiments of the invention will now be described, with reference to the Figures, in which:

FIG. 3 depicts, schematically, lock stitch attaching a material to the wall of a graft;

FIG. 4 is a schematic view of a lock stitch being formed in the wall of a graft;

FIG. 5A is a perspective view of a bobbin for use in the invention;

FIG. 5B is a perspective view of an alternative form of a bobbin for use in the invention;

DETAILED DESCRIPTION OF PREFERRED VERSIONS OF THE INVENTION

Figure 1A:
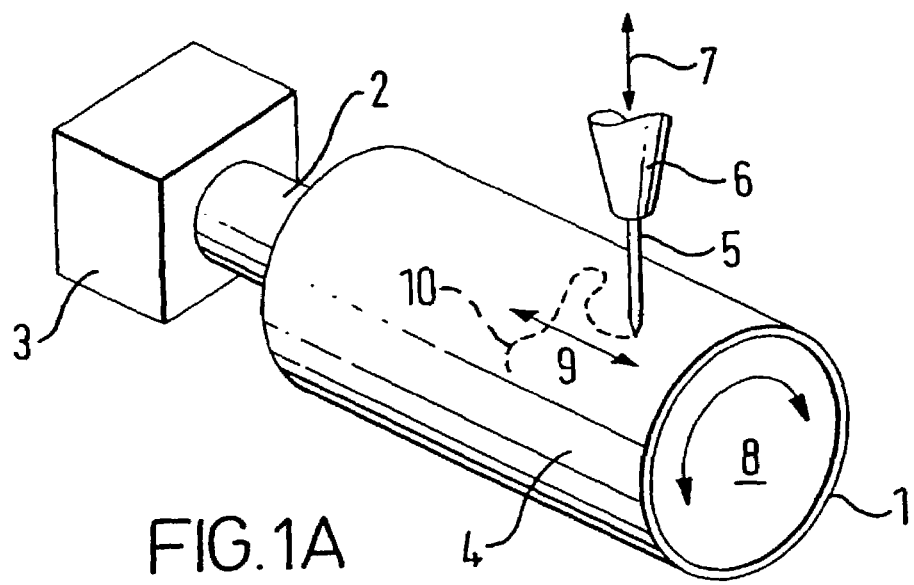
FIG. 1A shows a perspective schematic view of apparatus in accordance with the invention.

FIG. 1A shows a drum assembly 1 mounted on a rotor 2 which is driven by a drive assembly 3. A graft 4 is supported on drum assembly 1. Needle 5 is mounted on sewing machine head 6 above graft 4.

In operation, drive assembly 3 operates to rotate rotor 2, drum assembly 1 and graft 4 about the longitudinal axis of graft 4 as shown by arrow 8. Drive assembly 3 can also operate to translate graft 4 back and forth along its longitudinal axis as shown by arrow 9.

Sewing machine head 6 can be moved up and down relative to graft 4 as shown by arrow 7 by a drive system on the sewing machine (not shown). Thus a combination of these movements can be used to move needle 5 along the surface of graft 4 as shown by dotted line 10.

Figure 1B:
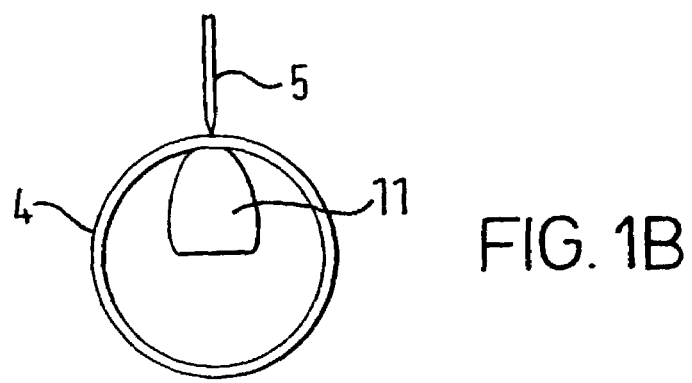
FIG. 1B shows an end view of the apparatus of FIG. 1A.

FIG. 1B shows an end-on view of the apparatus of FIG. 1A. Bobbin 11 can be seen inside graft 4 underneath needle 5. In operation, bobbin 11 can be moved back and forth along the longitudinal axis of graft 4 by a drive mechanism (not shown) in order to pass through loops of thread formed by needle 5.

Figure 2:
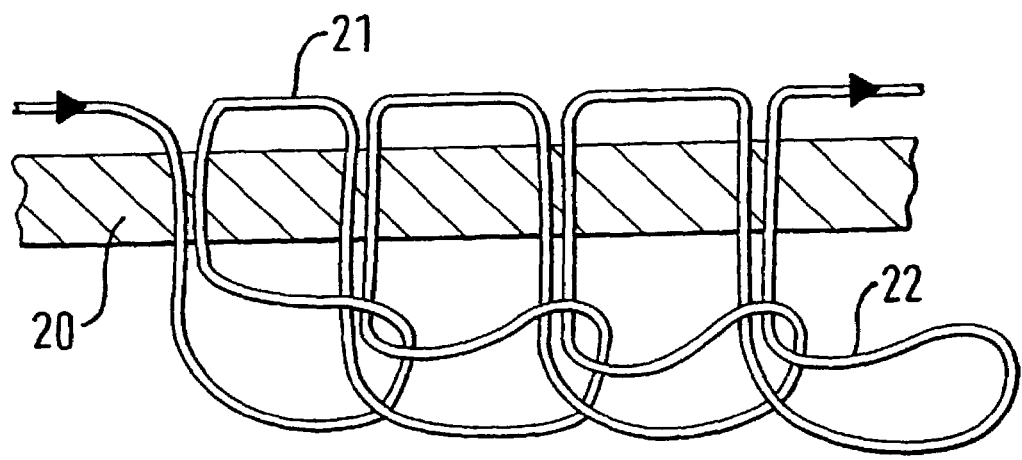
FIG. 2 depicts, schematically, chain stitch through the wall of a graft.

FIG. 2 shows graft wall 20 and the path of thread 21 through graft wall 20 to form a chain stitch 22.

FIG. 3 shows graft wall 30 and material 31 which has been stitched to graft wall 30 by passing top thread 32 through the materials and passing bottom thread 33 through loops formed in top thread 32 to form a lock stitch.

The process for forming a lock stitch in graft wall 30 is shown in more detail in FIG. 4. As can be seen, needle 5 with top thread 32 threaded therethrough punctures graft wall 30 to form a loop 40 inside the graft. Bottom thread 33 (not shown) can then be fed through loop 40 on a bobbin (not shown) in the direction of arrow 41. Afterwards, needle 5 can be removed to pull loop 40 closed to form the lock stitch.

FIGS. 5A and 5B show alternative embodiments of an elongate bobbin which can be used to form a lock stitch in accordance with the invention. FIG. 5A depicts cylindrical bobbin 51 which is mounted on axis 52 with thread 50 wound circumferentially around bobbin 51 to form turns 53. The alternative bobbin of FIG. 5B comprises a belt 54 mounted on rollers 55 in order to move back and forth along the longitudinal axis of the bobbin. Thread 50 can therefore be wound end to end on the bobbin to form turns 53.

Figure 6:
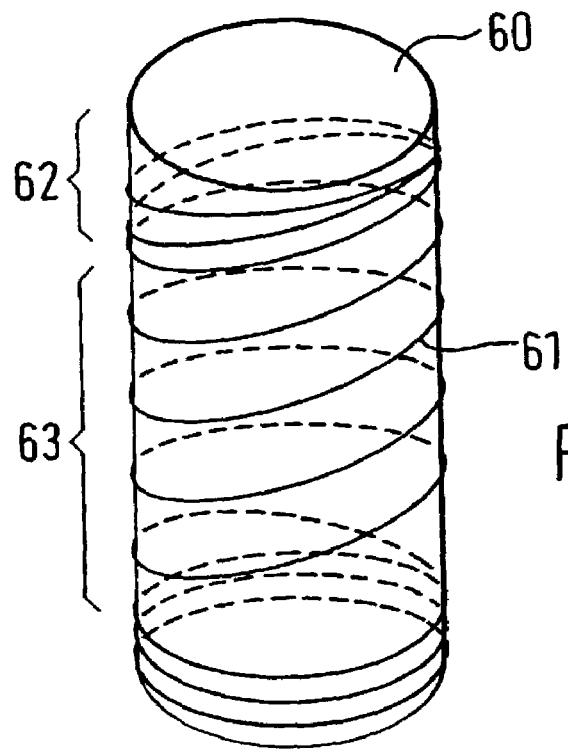
FIG. 6 shows a graft-stent in perspective and partial cut-away which has been formed by using a method according to the invention.

FIG. 6 shows graft-stent 60 with reinforcement wire 61 stitched to the tubular graft in a spiral formation (stitches not shown). The pitch of the spiral can be varied to create a region 62 in which reinforcement wire is packed densely, and region 63 which is less dense. Region 62 is therefore more reinforced than region 63, and so region 62 provides more support than region 63. However, the less dense packing of region 63 enables the graft-stent 60 to bend at that region around corners.

Figure 7:
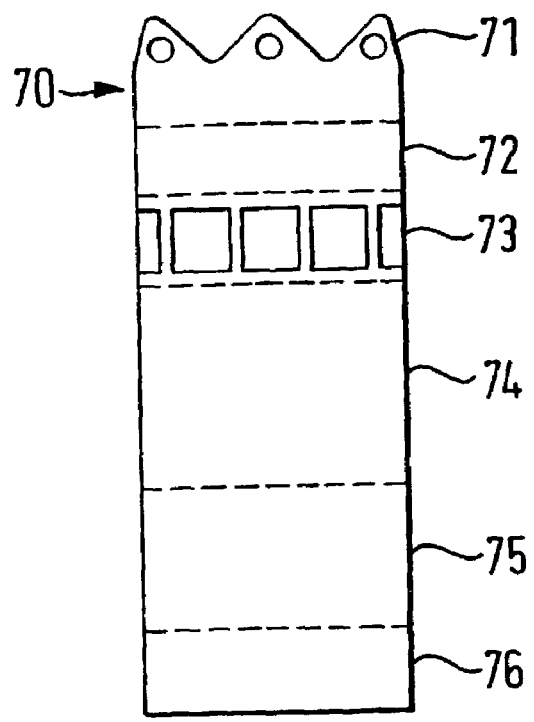
FIG. 7 shows a plan view of a graft with different regions which has been formed in accordance with the invention.

FIG. 7 shows graft-stent 70 which can be formed by method in accordance with the invention. Graft-stent 70 has a plurality of different regions, namely fixation region 71, dense region 72, fenestrated region 73, less dense region 74, region 75 on which different support elements can be mounted and region 76 on which barbs can be mounted (not shown).

The invention claimed is:

1. A method for stitching thread to the wall of a tubular medical implant, comprising the steps of:
   a. mounting the implant on an implant support,
   b. rotating and translating the implant support about and along its longitudinal axis in order to position a needle at any desired location over the implant surface,
   c. operating the needle to feed a first thread from a first side of the implant wall through the implant wall, wherein said first side of the implant wall is the outside of the implant,
   d. forming a first loop of the first thread on the second side of the implant wall, wherein said second side is the inside of the implant,
   e. passing thread through said loop, and
   f. pulling said loop closed to form a stitch,
   wherein the step of passing thread through said loop is carried out by means for passing thread through said loop, said means being driven back and forth along the longitudinal axis of the implant.

2. A method as claimed in claim 1, in which the thread which is passed through the first loop is a second loop of the first thread which has been fed through the wall of the implant, said second loop subsequently having a third loop of the first thread passed through it, in order to form a chain stitch in the implant wall.

3. A method as claimed in claim 1, in which the thread which is passed through said loop is a second thread which is subsequently passed through subsequent loops of the first thread which have been fed through the wall of the implant, in order to form a lock stitch in the implant wall.

4. A method as claimed in claim 1, wherein an elongate element is employed inside the implant to pass said thread through said first loop, the elongate element being operable from outside the implant.

5. A method as claimed in claim 4, wherein the elongate element comprises an elongate bobbin or hook.

6. Apparatus for stitching thread to the wall of a tubular medical implant, comprising:
   a. a support for the implant,
   b. a needle for feeding a first head from a first side of the implant wall through the implant wall to form a first loop of thread on the second side of the implant wall, wherein said first side of the implant wall is the outside of the implant,
   c. means for passing thread through said loop from the second side of the implant wall, wherein said second side is the inside of the implant,
   d. at least one drive mechanism for rotating and translating the implant support about and along its longitudinal axis in order to position the needle at any desired location over the implant surface, and
   e. a further drive mechanism for driving said means for passing thread trough said loop back and forth along the longitudinal axis of the implant.

7. Apparatus as claimed in claim 6, comprising an elongate element for passing said thread through said first loop, the elongate element being operable from outside the implant.

8. Apparatus as claimed in claim 7, wherein the elongate element comprises an elongate bobbin or hook.

9. Apparatus as claimed in claim 6, wherein the implant support is a hollow drum assembly for supporting the implant at either end.

10. A method for stitching thread to the wall of a tubular medical implant, comprising the steps of:
   a. mounting the implant on an elongated implant support,
   b. rotating and translating the implant support about and along its longitudinal axis in order to position a needle at a desired location over the surface of the implant,
   c. operating a needle to feed a first thread through a first side of the implant wall, wherein said first side of the implant wall is the outside of the implant,
   d. forming a loop of the first thread on the second side of the implant wall, wherein said second side is the inside of the implant,
   e. passing thread through said loop with a bobbin or hook, and pulling said loop closed to form a stitch,
   wherein the bobbin or hook is driven along the longitudinal axis of the implant.

* * * * *